United States Patent
Black

(10) Patent No.: US 9,394,232 B2
(45) Date of Patent: Jul. 19, 2016

(54) COST EFFECTIVE METHOD OF PRODUCING TRIARYLAMINE COMPOUNDS HAVING TWO ALKLY ALCOHOLS

(71) Applicant: David Glenn Black, Broomfield, CO (US)

(72) Inventor: David Glenn Black, Broomfield, CO (US)

(73) Assignee: LEXMARK INTERNATIONAL, INC., Lexington, KY (US)

( * ) Notice: Subject to any disclaimer, the term of this patent is extended or adjusted under 35 U.S.C. 154(b) by 0 days.

(21) Appl. No.: 14/104,122

(22) Filed: Dec. 12, 2013

(65) Prior Publication Data

US 2015/0166463 A1    Jun. 18, 2015

(51) Int. Cl.
    *C07C 213/02* (2006.01)
(52) U.S. Cl.
    CPC .................................. *C07C 213/02* (2013.01)
(58) Field of Classification Search
    CPC .................................................... C07C 213/02
    See application file for complete search history.

(56) References Cited

U.S. PATENT DOCUMENTS 7,482,492 B2 * 1/2009 Coggan et al. ............... 564/405

OTHER PUBLICATIONS

Buchwald et al. J. Org. Chem. 2000, 65, 5327-5333.*
Buchwald et al. J. Am. Chem. Soc. 129 (16), 2007, 5096-5101.*

* cited by examiner

*Primary Examiner* — Clinton Brooks

(57) ABSTRACT

The present invention provides a simple, cost effective and time saving one step method for synthesizing triarylamines comprising two alkyl alcohol without the need for the protection and the deprotection steps. More particularly, the invention provides an improved method of producing triarylamine compounds having two alkyl alcohol groups by reaction of a primary arylamine (aniline) with a halogenated aryl alkyl alcohol. The reaction proceeds in one step, whereby a primary arylamine is reacted with two equivalents of a halogenated aryl alkyl alcohol in the presence of a catalytic amount of palladium, ligand, solvent and base.

16 Claims, No Drawings

COST EFFECTIVE METHOD OF PRODUCING TRIARYLAMINE COMPOUNDS HAVING TWO ALKLY ALCOHOLS

STATEMENT REGARDING FEDERALLY SPONSORED RESEARCH OR DEVELOPMENT

None.

REFERENCE TO SEQUENTIAL LISTING, ETC.

None.

BACKGROUND

1. Field of the Invention

The present invention relates to an electrophotographic (EP) photoreceptor within an EP printer. More particularly, the invention relates to an improved method for the production of triarylamine compounds comprising two alkyl alcohol groups. The resulting triarylamine alkyl alcohols are important for use as the starting materials for synthesis of triarylamine compounds comprising two crosslinkable group.

2. Description of the Related Art

An EP printer, such as a laser printer, is comprised of a print engine and a replaceable EP process cartridge. The replaceable process cartridge supplies toner, as well other wearing components necessary for the electrophotographic process. The photoreceptor is generally thought of as a replaceable supply item, but may be found within either the print engine, or in the process cartridge.

In electrophotography, a latent image is created on the surface of an imaging member such as a photoconducting material by selectively exposing areas of the surface to light. A difference in electrostatic charge density is created between those areas on the surface which are exposed to light and those areas on the surface which are not exposed to light. The latent electrostatic image is developed into a visible image by electrostatic toners. The toners are selectively attracted to either the exposed or unexposed portions of the photoconductor surface, depending on the relative electrostatic charges on the photoconductor surface, the development electrode and the toner.

Although organic electrophotographic photoconductors may be of single layer construction, many organic photoconductors have a dual layer construction. Dual layer photoconductors typically comprise a substrate such as a metal ground plane member on which a charge generation layer and a charge transport layer are coated. When the charge transport layer is formed on the charge generation layer, the photoconductor exhibits a negative charge on its surface. Conversely, when the charge generation layer is formed on the charge transport layer, the photoconductor exhibits a positive charge on the surface. Unless otherwise noted, the present disclosure addresses negative charging photoconductors. Conventionally, the charge generation layer comprises a polymeric binder containing a charge generating compound or molecule while the charge transport layer comprises a polymeric binder containing a charge transport compound or molecule. The charge generating compounds within the charge generation layer are sensitive to image-forming radiation and photogenerate free electron-hole pairs within the charge generation layer as a result of such radiation. The charge transport layer is usually non-absorbent of the image-forming radiation and the charge transport compounds serve to transport holes to the surface of the photoconductor.

One problem associated with some organic photoconductors is that their wear performance is generally inferior to that of inorganic photoconductors, such as amorphous silicon. Photoreceptor wear in the print area is either roughly uniform or non-uniform in nature. This latter wear mechanism often appears as gouges or scratches on the photoreceptor surface, which may manifest themselves as defects in the printed product. Even thin scratches can result in a general print lightning when present in a sufficient density. Concurrent with the appearance of scratches is a general abrasion of the charge transport layer (or charge generation layer when charging positively). The thickness loss changes the electrical properties of the photoreceptor by (1) changing the capacitance and (2) decreasing the transit time required for holes to discharge the surface. This abrasive wear results from interaction of the photoreceptor with other EP components such as toner, cleaner blade and paper.

Providing photoreceptors with a high degree of electrical stability over cartridge life is one goal of the photoreceptor development community. Another important goal is to provide photoreceptors with exceptionally long lives such as greater than 100 k prints. Heretofore it has been difficult to develop a photoreceptor which can meet these two goals simultaneously. One tried route to achieving both of these goals is the application of a crosslinkable protective coating as the outermost layer of the photoreceptor. However, abrasion resistant crosslinkable monomers, oligomers and polymers are generally electrically insulating. Photoreceptors must be insulating in the dark, but conductive when exposed to light. Depositing an insulating layer on the surface of the photoreceptor prevents charge migration, and thus prevents generation of the electrical contrast required to tone an image. One way of combining both high abrasion resistance and proper electrical properties includes forming overcoats comprising charge transport molecules further comprising crosslinkable functional groups. The resulting crosslinked layer, typically 3-5 µm thick, is highly resistant to thickness loss and therefore demonstrates much greater electrical stability than a non-overcoated photoreceptor. A photoreceptor overcoat comprising a UV crosslinked layer of hexacoordinate urethane acrylate and UV crosslinkable charge transport molecule is disclosed in U.S. patent application Ser. No. 13/731,594 entitled "Photo Conductor Overcoats Comprising Radical Polymerizable Charge Transport Molecules and Hexa-Functional Urethane Acrylates", which is assigned to the assignee of the present application and is incorporated by reference herein in its entirety.

The most commonly used charge transport molecule used in modern laser printers are triarylamines. Production of arylamine hole transport compounds require the synthesis of intermediate materials, which are costly and/or time-consuming to produce, and some of which require a multi-step manufacturing process. For example, diarylamines may be produced using traditional Goldberg reactions. This method requires the derivatization of an aniline with acetic anhydride to produce an acetanilide compound. The acetanilide compound is then reacted with an arylbromide compound to produce an intermediate that must then be hydrolyzed in alcohol solution to produce the diarylamine compound. The formation of diphenylamines using the Goldberg reaction takes three reaction steps, and thus can be a lengthy process. Total cycle time for this process can be 3 to 5 days in the lab. Diarylamines may also be produced by subjecting an arylamine to condensation reaction in the co-presence of anhydrous aluminum chloride and anhydrous calcium chloride. Both of these methods require high temperatures and harsh reaction conditions. The purity of the diarylamines obtained from these two reactions are generally low, requiring lengthy and costly purification processes. The resulting diarylamines may be reacted with halogenated aryl compounds to form a variety of triarylamine compounds.

Until recently, the most common method of producing triphenylamines was the Ullman reaction. Ullman coupling chemistry has been known for over one hundred years and generally involves reaction of an amine with an aryl iodide in the presence of copper. The Ullman reaction suffers from the following drawbacks: (1) aryl iodide compounds are generally more expensive than their bromide or chloride analogues, (2) the reaction uses large, sometimes stoichiometric, amounts of copper and is thus not environmentally friendly, (3) the reaction temperature is often very high and thus requires use of high boiling and hazardous solvents such as dichlorobenzene and high boiling solvents are notoriously difficult to remove, (4) the reaction often produces side products that may be difficult to remove by standard purification methods: and (5) Ullman chemistry does not allow the presence of protic functional groups such as alcohols.

The last 20 years have seen the development of an alternative to the Goldberg and Ullman reactions. The Buchwald-Hartwig reaction allows for production of di- and triarylamine compounds by coupling an arylamine with an aryl halide in the presence of a ligated palladium catalyst and base. Buchwald-Hartwig chemistry has at least four advantages over the Goldberg and Ullman reactions discussed above. (1) The process allows for use of aryl bromide and chloride reagents and thus represents an immediate cost reduction. (2) Very low catalyst loadings, sometimes as low as 0.05%, are required and may thus be viewed as environmentally friendly. (3) The reaction is performed in relatively low boiling solvents such as THF or toluene that are easily removed by vacuum distillation. (4) The reaction provides both high yields and high purity.

Formation of triarylamines comprising at least one alkyl hydroxy group according to the methods cited above requires protection of the hydroxy group(s). The hydroxy group is the most common precursor for incorporation of crosslinkable groups, such as acrylates, to molecules. Protection is required since alcohols, as well as other protic functional groups, can interfere with the triphenylamine synthesis. Alcohol protection adds two synthesis/purification steps (protection and deprotection) to the synthesis and is thus unproductive.

In a general sense, the photoreceptor is called upon to create (with the image writing light source), develop, and transfer a latent image to a substrate. In large part, the electrical changes that occur to a photoreceptor throughout print life are a result of charge transport layer thickness changes induced by abrasion with other components of the EP system. Addition of a crosslinkable overcoat layer that combines excellent wear resistance with the semi conductive properties of a photoreceptor greatly increases the useful life of the photoreceptor while also improving the electrical stability. Current methods for preparing charge transport molecules, such as triarylamines, incorporating alkyl alcohols are inefficient, time consuming, and costly. The primary reason for the deficiency in making triarylamines including alkyl alcohols is the need to include the necessary protection and deprotection steps to the synthesis of triarylamines incorporating alkyl alcohols. Using the alkyl alcohol as a starting material, crosslinkable functionality may be incorporated using well known methods such as reacting the alkyl alcohol with acryloyl chloride in the presence of a base such as diethylamine. Consequently, an efficient method for producing triarylamines incorporating alkyl alcohols remains an unmet need within the electrophotographic arts.

SUMMARY OF THE INVENTION

The present invention provides a simple, cost effective and time saving one step method for synthesizing triarylamines comprising two alkyl alcohol without the need for the protection and the deprotection steps. More particularly, the invention provides an improved method of producing triarylamine compounds having two alkyl alcohol groups by reaction of a primary arylamine (aniline) with a halogenated aryl alkyl alcohol. The reaction proceeds in one step, whereby a primary arylamine is reacted with two equivalents of a halogenated aryl alkyl alcohol in the presence of a catalytic amount of palladium, ligand, solvent and base. These materials are excellent precursors for synthesis of triarylamines comprising two crosslinkable groups. As such, these triarylamines comprising two crosslinkable groups can then be incorporated into an effective overcoat for an organic photoconductor or 'OPC'.

These and additional objects and advantages provided by the embodiments of the present invention will be more fully understood in view of the following detailed description, in conjunction with the drawings.

DETAILED DESCRIPTION

This disclosure is not limited to particular embodiments described herein, and some components and processes may be varied by one of skill, based on this disclosure. The terminology used herein is for the purpose of describing particular embodiments only, and is not intended to be limiting.

In this specification and the claims that follow, singular forms such as "a," "an," and "the" include plural forms unless the content clearly dictates otherwise. In addition, reference may be made to a number of terms that shall be defined as follows:

An animation is the process of reacting an N—H bond with an organic molecule to form a N—C bond. The carbon may be an alkyl carbon or an aryl carbon. The Buchwald-Hartwig animation is the process of reacting an N—H group with an aryl halide to form a N-aryl bond wherein the nitrogen is bonded directly to a carbon of an aryl group. The terms "Buchwald-Hartwig animation" and "Buchwald-Hartwig reaction" may be used interchangeably.

The term "aryl" refers to a monocyclic aromatic species of about 6 to about 20 carbon atoms or more, such as phenyl, naphthyl, anthrycyl, and the like. Optionally, these groups may be substituted with one or more independently selected substituents, including alkyl, alkenyl, alkoxy, and nitro groups. "Ar" is shorthand for the aryl group.

The terms "hydrocarbon" and "alkane" refer, for example, to branched and unbranched molecules having the general formula $C_nH_{2n+2}$, wherein n is, for example, a number from 1 to about 100 or more, such as methane, ethane, n-propane, isopropane, n-butane, isobutane, tert-butane, octane, decane, tetradecane, hexadecane, eicosane, tetracosane, and the like. Alkanes may be substituted by replacing hydrogen atoms with one or more functional groups. The term "aliphatic" refers, for example, to straight-chain molecules, and may be used to describe acyclic, unbranched alkanes. The term "long-chain" refers, for example, to hydrocarbon chains in which n is a number of from about 8 to about 60, such as from about 20 to about 45 or from about 30 to about 40. The term "short-chain" refers, for example, to hydrocarbon chains in which n is an integer of from about 1 to about 7, such as from about 2 to about 5 or from about 3 to about 4.

The term "alkyl" refers, for example, to a branched or unbranched saturated hydrocarbon group having one substituent and derived from an alkane and having the general formula $C_nH_{2n+1}$, wherein n is, for example, a number from 1 to about 100 or more, such as methyl, ethyl, n-propyl isopropyl, n-butyl, isobutyl, tert-butyl, octyl, decyl, tetradecyl, hexadecyl, eicosyl, tetracosyl, and the like. An example of an alkyl group having the general formula $C_nH_{2n+1}$ is $(C_2H_5)$—OH. An alkyl group having two substituents has the general formula $C_nH_{2n}$. An example of which $Ar(C_2H_4)$—OH. The term "lower alkyl" refers, for example, to an alkyl group of from about 1 to about 12 carbon atoms. "Halogenated alkyl" refers, for example, to an alkyl group in which at least one hydrogen atom, and optionally all hydrogen atoms, is replaced by a halogen atom.

The term "arylamine" refers, for example, to moieties containing both aryl and amine groups. Exemplary aralkylene groups have the structure Ar—NRR', in which Ar represents an aryl group and R and R' are groups that may be independently selected from hydrogen and substituted and unsubstituted alkyl, alkenyl, aryl, and other suitable functional groups. The term "primary arylamine" may be used interchangeably with "aniline," since both refer to compounds possessing the general structure $H_2N$—Ar. The term "triarylamine" refers, for example, to arylamine compounds having the general structure NArAr'Ar", in which Ar, Ar' and Ar" represent independently selected aryl groups.

The term "organic molecule" refers, for example, to any molecule that is made up predominantly of carbon and hydrogen, such as, for example, alkanes and arylamines. The term "heteroatom" refers, for example, to any atom other than carbon and hydrogen. Typical heteroatoms included in organic molecules include oxygen, nitrogen, sulfur and the like.

The term "alcohol" refers, for example, to an alkyl group in which one or more of the hydrogen atoms has been replaced by an "OH" group. The terms "alcohol" and "hydroxy" may be used interchangeably. The term "lower alcohol" refers, for example, to an alkyl group of about 1 to about 6 carbon atoms in which at least one, and optionally all, of the hydrogen atoms has been replaced by an —OH group.

The term "primary alcohol" refers to an alcohol attached to a carbon that is bonded to only one other carbon atom. This type of alcohol is also called a terminal alcohol since it is bonded to the last carbon in an alkyl chain. The term "secondary alcohol" refers to an alcohol that is attached to a carbon that is bonded to two other carbon atoms.

The term "halogenated aryl alkyl alcohol" refers to compounds having the general structure X—Ar($C_nH_{2n}$)—OH, where X represents a halogen, atom and $C_nH_{2n}$ refers to an alkyl group.

"Amine" refers, for example, to an alkyl moiety in which one or more of the hydrogen atoms has been replaced by an —$NH_2$ group. The term "lower amine" refers, for example, to an alkyl group of about 1 to about 6 carbon, atoms in which at least one, and optionally all, of the hydrogen atoms has been replaced by an —$NH_2$ group.

The term "derivative" refers, for example, to compounds that are derived from another compound and maintain the same general structure as the compound from which they are derived. For example, saturated alcohols and saturated amines are derivatives of alkanes.

The term, "analogous" refers, for example, to any number of series of organic compounds that have similar chemical properties and that differ by a constant relative molecular mass. For example, Cl—Ar and Br—Ar are analogous compounds because they are both halogen-substituted aryl compounds.

The term "ion" refers to atoms that bear a charge by virtue of an excess (negative charge) or deficiency (positive charge) of electrons required to give a charge of 0 and is based on the atomic number of the element.

The term "saturated" refers, for example, in compounds containing only single bonds. The term "unsaturated" refers, for example, to compounds that contain one or more double bonds and/or one or more triple bonds.

The term "reflux" refers, for example, to the process of boiling a liquid, condensing the vapor and returning the vapor to the original container. When a liquid is refluxed, the temperature of the boiling liquid remains constant. The term "boiling point" refers, for example, to the temperature at which the saturated vapor pressure of a liquid is equal to the external atmospheric pressure.

The terms "one or more" and "at least one" herein mean that the description includes instances in which one of the subsequently described circumstances occurs, and that the description includes instances in which more than one of the subsequently described circumstances occurs.

An improved method for producing triarylamines directly from a primary arylamine and a halogenated aryl alkyl alcohol is provided herein. The reaction proceeds in one step whereby a primary arylamine is reacted with two equivalents of a halogenated aryl alkyl alcohol in the presence of a catalytic amount of palladium, ligand, solvent and base. Performing the reaction in one step as opposed to three steps saves time and money. Fewer reaction steps also leads to higher yields. Additionally, a one vessel or pot reaction is much more convenient than the three vessels required in standard procedures.

The result is surprising since the preparation of triarylamines comprising one or more alcohol groups using previous methods included the costly and time consuming alcohol protection and deprotection steps. Without wishing to be bound by theory, one possibility for the alcohol protection requirement is that deprotonation of the alcohol in the presence of base gives a reactive alkoxide that can react with the palladium catalyst. Protection of the alcohol with a functional group that is impervious to the basic conditions of the reaction prevents this reaction pathway. Upon completion of the Buchwald-Hartwig animation, the protecting group may be removed to regenerate the alcohol functionality. Following the method of the present invention eliminates this costly and time consuming alcohol protection/deprotection process. Therefore, this process is very practical and applicable to the industrial scale preparation of triarylamines comprising one or more alkyl alcohol functional groups. This shorter, improved process is now described in detail.

Equations 1-3 below show a conventional three-step process for preparing a triarylamine comprising two alkyl alcohol functional groups.

Equation 1

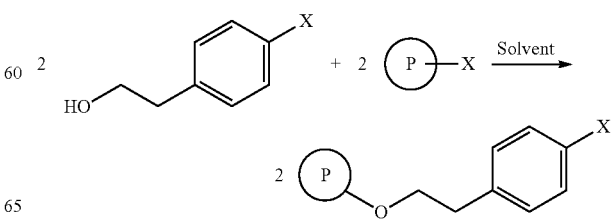

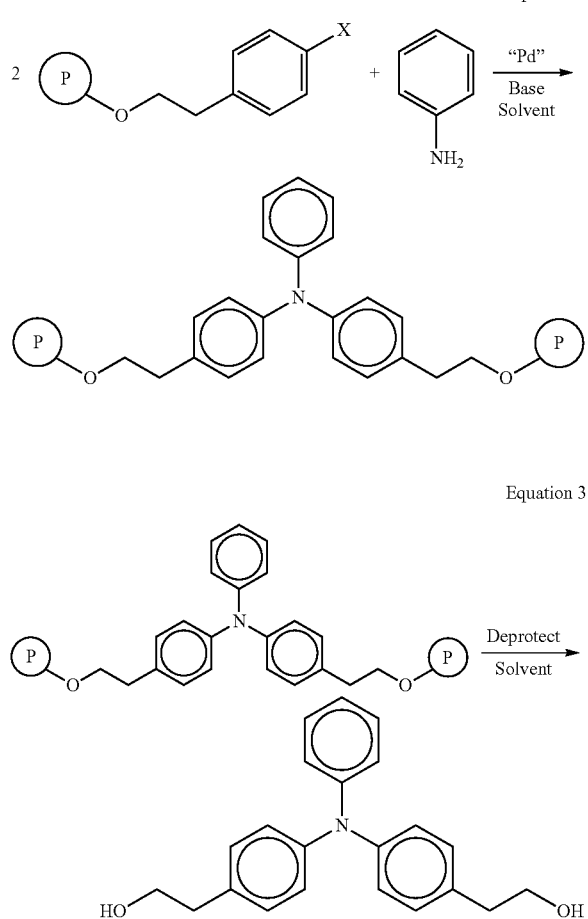

Equation 4 below shows the one-step method of the present invention for preparing the same triphenylamine.

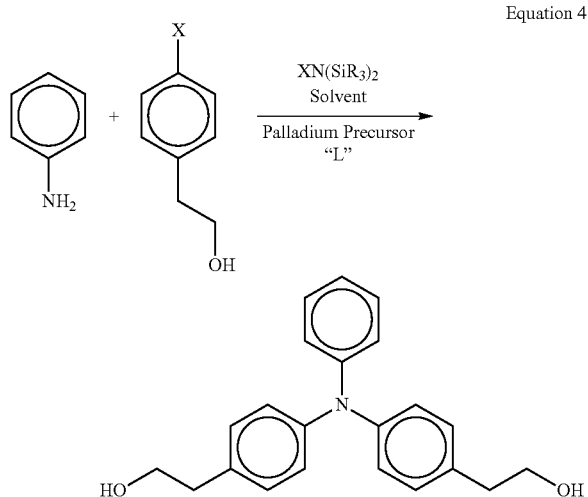

The base suitable for use in the present invention comprises an alkaline metal salt of a bis(trialkylsilyl)amide, represented by the general formula $MN(SiR_3)_2$, here M is an alkaline metal, N is a nitrogen atom and R is an alkyl group. In one embodiment, M is any alkaline metal ion. In another embodiment, M is selected from the list metal ions including lithium, sodium, and potassium. In another embodiment, M is lithium. In one embodiment, R is a lower alkyl group containing between 1 and about 12 carbon atoms. In another embodiment, R is a methyl group. The bis(trialkylsilyl)amide base may be purchased or prepared and used as a solid or a solution in an organic solvent.

The primary arylamine can be any suitable primary arylamine having the general formula $H_2N-Ar^1$. $Ar^1$ independently represents any known substituted or unsubstituted aromatic component or a substituted or unsubstituted aryl group having from 2 to about 15 conjugate bonded or fused benzene rings and could include, but is not limited to, phenyl, naphthyl, anthryl, phenanthryl, and the like. The substituents on $Ar^1$ can be suitably selected to represent hydrogen, a halogen, an alkyl group having from 1 to about 20 carbon atoms, a hydrocarbon radical having from 1 to about 20 carbon atoms, an aryl group optionally substituted by one or more alkyl groups, an alkyl group containing a heteroatom such as oxygen, nitrogen, sulfur, and the like, having from 1 to about 20 carbon atoms, a hydrocarbon radical containing a heteroatom such as oxygen, nitrogen, sulfur, and the like, having from 1 to about 20 carbon atoms, an aryl group containing a heteroatom such as oxygen, nitrogen, sulfur, and the like, optionally substituted by one or more alkyl groups, and the like.

The aryl alkyl alcohol can be any suitable aryl alkyl alcohol having the general formula $X-Ar^2((C_nH_{2n})-OH)_2$. X represents any suitable halide that is reactive in the Buchwald-Hartwig animation. In one embodiment, the halide is selected from the list including chloride, bromide and iodide. In another embodiment, the halide is selected from chlorine and bromine. In another embodiment the halide is chlorine. $Ar^2$ represents any known substituted or unsubstituted aromatic component or a substituted or unsubstituted aryl group having from 2 to about 15 conjugate bonded or fused benzene rings and could include, but is not limited to, phenyl, naphthyl, anthryl, phenanthryl, and the like. The substituents on $Ar^2$ can be suitably selected to represent hydrogen, a halogen, an alkyl group having from 1 to about 20 carbon atoms, a hydrocarbon radical having from 1 to about 20 carbon atoms, an aryl group optionally substituted by one or more alkyl groups, an alkyl group containing a heteroatom such as oxygen, nitrogen, sulfur, and the like, having from 1 to about 20 carbon atoms, a hydrocarbon radical containing a heteroatom such as oxygen, nitrogen, sulfur, and the like, having from 1 to about 20 carbon atoms, an aryl group containing a heteroatom such as oxygen, nitrogen, sulfur, and the like, optionally substituted by one or more alkyl groups, and the like. One of the substituents bonded to $Ar^2$ is an alkyl alcohol represented by the general formula $(C_nH_{2n})-OH$. In principle, the alkyl group, $C_nH_{2n}$, is any branched or unbranched saturated hydrocarbon wherein n is, for example, a number between 1 and 100. In one embodiment, the alkyl group is a lower alkyl with a value of n between 1 and 12. In another embodiment, the value of n is between 1 and 6. In yet another embodiment, the value of n is between 2 and 4. In principle, the alkyl alcohol group may reside in the ortho, meta, or para position relative to the halide. However, the inventors have found that only substitution at the para position provides the electrical properties necessary for use in an organic photoreceptor.

The alcohol of the alkyl alcohol may be a primary alcohol, a secondary alcohol, or a mixture thereof. In one embodiment, both of the alcohol groups of the of the alkyl alcohol are primary alcohols. In a second embodiment, both of the alcohol groups of the of the alkyl alcohol are secondary alcohols.

The palladium precursor is any source of palladium capable of catalyzing the Buchwald-Hartwig reaction in the presence of the appropriate ligand. The palladium precursor should have an oxidation state of 0, 'Pd(0)', or be capable of being reduced to Pd(0) under the reaction conditions. In the event that the palladium precursor is not Pd(0), but rather for example, 'Pd(II)', addition of a small amounts reducing agent such as a tertiary amine or boronic acid may be required to generate Pd(0). Pd(II) refers to the +2 oxidation state of palladium, Pd(II) will not lead to a functional catalyst for the present invention. Addition of small amounts of reducing agent(s) such as triethylamine or phenyl boronic acid which are required to reduce Pd(II) to Pd(0) are regarded as failing within the scope of the present invention. Examples of Pd(0) sources include, but are not limited to tris(dibenzylideneacetone)dipalladium ($Pd_2(dba)_3$), and di(dibenzylideneacetone)palladium ($Pd(dba)_2$). Sources of Pd(II) include, but are not limited to palladium chloride, palladium bromide, palladium iodide, palladium acetate, palladium acetylacetonate, palladium hexafluoroacetylacetonate, palladium trifluoroacetate, allyl palladium chloride dimer, (2,2'-bipyridine)dichloropalladium, bis(benzonitrile)dichloropalladium, bis(acetonitrile)dichloropalladium, (bicyclo[2,2,1]hepta-2,5-diene)dichloropalladium, dichloro(1,5-cyclooctadiene)palladium, dibromobis(triphenylphosphine)palladium, dichloro(N,N,N',N'-tetramethylethylenediamine)palladium, dichloro(1,10-phenathroline)palladium, dichlorobis(triphenylphosphinepalladium), ammonium tetrachloropalladate, diaminedibromopalladium, diaminedichloropalladium, diaminediiodopalladium, potassium tetrabromopalladate, potassium tetrachloropalladate and sodium tetrachloropalladate. In one aspect, the palladium precursor is chosen from tris(dibenzylideneacetone)dipalladium, and palladium acetate. In another embodiment, the palladium precursor is tris(dibenzylideneacetone)dipalladium.

The ligand is any molecule capable of coordinating to the palladium precursor and facilitating the Buchwald-Hartwig reaction. These ligands include, but are not limited to dialkylbiarylphosphines, ferrocenyl diphenyl and dialkyl phosphines and bulky, electron rich phosophines. Examples of dialkylbiarylphosphine ligands include: 2-Dicyclohexylphosphino-2'-(N,N-dimethylamino)biphenyl (DavePhos), 2-Dicyclohexylphosphino-2',4',6'-triisopropylbiphenyl (Xphos), 2-Dicyclohexylphosphino-2',6'-dimethoxybiphenyl (Sphos), 2-Di-tert-butylphosphino-2',4',6'-triisopropylbiphenyl (tBuXPhos), (2-Biphenyl)dicyclohexylphosphine, 2-(dicyclohexylphosphino)biphenyl (CyJohnPhos), (2-Biphenyl)di-tert-butylphosphine (JohnPhos), 2-dicyclohexylphosphino-2',6'-diisopropoxybiphenyl (RuPhos), 2-Di-tert-butylphosphino-2'-methylbiphenyl (tBuMePhos), 2-Di-tert-butylphosphino-3,4,5,6-tetramethyl-2',4',6'-triisopropyl-1,1'-biphenyl 2-Di-tert-butylphosphino-2'-methylbiphenyl (tBuMePhos), 2-Di-tert-butylphosphino-3,4,5,6-tetramethyl-2',4',6'-triisopropyl-1,1'-biphenyl (Tetramethyl tBuXPhos), and 2-(dicyclophexylphosphino)3,6-dimethoxy-2',4',6'-triisopropyl-1,1'-biphenyl (BrettPhos). Examples ferrocenyl diphenyl and dialkyl phosphines include: 1,1'-Ferrocenediyl-bis(diphenylphosphine) (DPPF), 1,2,3,4,5-Pentaphenyl-1'-(di-tert-butylphosphino)ferrocene (Q-Phos), 1,1'-Bis(di-tert-butylphosphino)ferrocene, 1,1'-Bis(dicyclohexylphosphino)ferrocene and 1,1'-Bis(diisopropylphosphino)ferrocene. An example of a bulky, electron rich phosphines are is tri tert-butylphosphine. Brett Phos is known to arylate primary arylamines to secondary arylamines, while RuPhos is known to arylate secondary amines to triarylamines. The inventor has surprisingly discovered that a combination of a BrettPhos ligand and a RuPhos ligand catalyzes the transformation of a primary arylamine to a triarylamine. In principle, the ratio of the two ligands is not limiting. Both ligands need to be present in order to generate a triarylamine from a primary arylamine. In the preferred embodiment, the ligand is a combination of BrettPhos and RuPhos. Preferably the ratio of the BrettPhos:RuPhos is about 1:4. In another embodiment, the ligand is tBuXPhos, and in another embodiment, the ligand is DPPF.

Any non-halogenated organic solvent may be used in the present invention, so long as it is free of moisture. Halogenated solvents may react in the Buchwald-Hartwig animation and thus lower the yield of the desired product. Water molecules react with the bis(trimethylsilyl)amide base and thus should be excluded from the solvent. Common organic solvents include, but are not limited to: cyclic ethers such as tetrahydrofuran (THF), ethers such as diethyl ether or tert-butyl methyl ether aromatic solvents such as toluene or xylene, acetate solvents such as ethyl acetate or butyl acetate, aliphatic solvents such as hexane or decane, and amide solvents such as dimethyl formamide (DMF), dimethyl acetamide (DMAc) and N-methylpyrrolidone (NMP). The bis(trialkylsilyl)amide base may be purchased as, for example, a 1M solution in an organic solvent. In this case, the reaction solvent comprises the same solvent as that used to solvate the bis(trialkylsilyl)amide base. Those skilled in the art will understand that the solvents exemplified above may be used alone or in combination. In one embodiment, the solvent is selected from the list including THF, tert-butyl methyl, hexane or toluene. In a second embodiment, the solvent is THF.

EXAMPLES

An oven dried 5 L round bottom flask equipped with a reflux condenser a gas inlet outlet valves was charged with 4-chlorophenethyl alcohol (52.6 g, 0.334 moles) and toluidine (16.8 g, 0.157 moles), lithium bis trimethylsilylamide (1 L, 1M) was then added via cannula transfer. The resulting dark brown slurry was stirred under nitrogen for 30 minutes. Under a strong stream of nitrogen, $Pd_2(dba)_3$ (1.1 g, 0.0012 moles), RuPhos (1.0 g, 2.1 mmole), and BrettPhos (0.3 g, 0.56 mmole) was added at once. The stopcock was immediately replaced and the flask was heated to reflux under nitrogen. After about 1.5 h, a dark blue solid began coating the flask.

The reaction was allowed to proceed overnight. The next morning, the inside of the flask was coated with a dark blue solid. The reaction was allowed to proceed for a total time of 22 h. The flask was cooled and 200 mL of toluene was added to the flask, 2M HCl was added dropwise until the mixture became acidic as judged by PH paper. Note that acid hydrolysis is exothermic. During the addition, the blue solid slowly dissolved. The resulting two-phase mixture was neutralized using a saturated solution of $NaHCO_3$. The organic layer was separated and washed with 2×200 mL of NaOH, and 3×3 300 mL of brine. The resulting dark brown solution was filtered through a short bed of alumina and dried over $MgSO_4$. Solvent was removed under vacuum to give a dark brown viscous liquid. Analysis by GC/MS showed that this material had a purity of 95.3%. Diethyl ether (25 mL) was slowly added and resulted in formation of a solid. The solid was filtered and washed with 1/1 diethyl ether/hexane (50 mL) and hexane (100 mL) to give a tan solid (35.4 g, 65.0% yield).

What is claimed is:
1. A method for forming triarylamine compounds comprising two alkyl alcohol groups comprising the steps of reacting a halogenated aryl alkyl alcohol with a primary aryl amine in the presence of a base having an alkaline metal salt of a bis(trialkylsilyl)amide, represented by the general formula $MN(SiR_3)_2$, wherein:
M is an lithium ion,
N is a nitrogen atom; and
R is an methyl group,
solvent, palladium precursor and ligand(s).

2. The method of claim 1, where in the halogenated aryl alkyl alcohol is represented as follows:

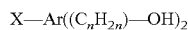

wherein:
X is a halogen,
Ar is an aryl group; and
$C_nH_{2n}$ is an alkyl group.

3. The method of claim 2, wherein Ar is a phenyl group.

4. The method of claim 2, wherein X is selected from the group consisting of chlorine, bromine and iodine.

5. The method of claim 4, wherein X is chlorine.

6. The method of claim 4, wherein X is bromine.

7. The method of claim 2 wherein $C_nH_{2n}$ is a lower alkyl group having between 1 and 12 carbon atoms.

8. The method of claim 2, wherein is $(C_nH_{2n})$—OH is a primary alkyl alcohol.

9. The method of claim 1, wherein the palladium precursor is selected from the group consisting of tris(dibenzylideneacetone)dipalladium ($Pd_2(dba)_3$) and palladium acetate.

10. The method of claim 9, wherein the palladium precursor is tris(dibenzylideneacetone)dipalladium ($Pd_2(dba)_3$).

11. The method of claim 1, wherein the ligand is selected from the group consisting of 2-Di-tert-butylphosphino-2',4',6'-triisopropylbiphenyl (tBuXPhos), 1,1'-Ferrocenediyl-bis(diphenylphosphine) (DPPF) and tri tert-butylphosphine.

12. The method of claim 11, wherein the ligand is 2-Di-tert-butylphosphino-2',4',6'-triisopropylbiphenyl (tBuXPhos).

13. The method of claim 1, wherein the ligand is a mixture of 2-Dicyclohexylphosphino-2',6'-diisopropoxybiphenyl (RuPhos) and 2-(Dicyclohexylphosphino)3,6-dimethoxy-2',4',6'-triisopropyl-1,1'-biphenyl (BrettPhos).

14. The method of claim 1, wherein the solvent is selected from the group consisting of: cyclic ethers such as tetrahydrofuran (THF), ethers such as diethyl ether or tert-butyl methyl ether, aromatic solvents such as toluene or xylene, acetate solvents such as ethyl acetate or butyl acetate, aliphatic solvents such as hexane or decane, and amide solvents such as dimethyl formamide (DMF), dimethyl acetamide (DMAc) and N-methylpyrrolidone (NMP).

15. The method of claim 14, wherein the solvent is tetrahydrofuran THF.

16. The method of claim 13 wherein the ratio of the of 2-Dicyclohexylphosphino-2',6'-diisopropoxybiphenyl (RuPhos) to 2-(Dicyclohexylphosphino)3,6-dimethoxy-2',4',6'-triisopropyl-1,1'-biphenyl (BrettPhos) is about 1:4.

* * * * *